United States Patent [19]
Breen et al.

[11] Patent Number: 5,792,173
[45] Date of Patent: Aug. 11, 1998

[54] WOUND CLOSURE HEMOSTASIS DEVICE

[75] Inventors: Richard C. Breen, Doncaster East;
Peter H. Lazarus, Templestowe, both of Australia; Stuart D. Edwards, 1681 Austin Ave., Los Altos, Calif. 94024; Edward J. Gough, San Carlos, Calif.

[73] Assignee: Stuart D. Edwards, Los Altos, Calif.

[21] Appl. No.: 500,381

[22] Filed: Jul. 10, 1995

[51] Int. Cl.⁶ .................................................. A61B 17/00
[52] U.S. Cl. .................................................. 606/201; 606/1
[58] Field of Search .................................... 606/190–200; 604/95–104; 666/201–204.55; 128/DIG. 20

[56] References Cited

U.S. PATENT DOCUMENTS

| 2,185,571 | 2/1940 | Robinson. | |
|---|---|---|---|
| 5,433,724 | 7/1995 | Kawasaki et al. | 606/202 |
| 5,486,194 | 1/1996 | Kawasaki et al. | 606/203 |

FOREIGN PATENT DOCUMENTS

| 140 861 | 9/1930 | China. | |
|---|---|---|---|
| 0 174 179 | 9/1985 | European Pat. Off.. | |
| 0462088 | 12/1991 | European Pat. Off. | 606/201 |
| 0 601 756 | 6/1994 | European Pat. Off.. | |
| 35 00 078 | 7/1985 | Germany. | |
| 87 15 460 | 1/1988 | Germany. | |
| 1 836 055 | 8/1993 | U.S.S.R.. | |
| 2 109 239 | 6/1983 | United Kingdom. | |

*Primary Examiner*—Glenn K. Dawson
*Attorney, Agent, or Firm*—Wilson, Sonsini, Goodrich and Rosati

[57] ABSTRACT

A wound closure, hemostasis device, such as a femoral hemostat, includes an inflatable balloon with an inflation and deflation outlet. A placement patch includes an aperture for receiving the inflation and deflation outlet. The inflatable balloon is coupled to the placement patch and positioned adjacent to a wound site or a bleeding vessel. A belt straps through the placement patch and around the patient's body or a patient's appendage and holds the placement patch at the wound site or bleeding vessel. An inflation tube is coupled to the inflation and deflation outlet. An inflation apparatus is coupled to the inflation and deflation outlet.

43 Claims, 10 Drawing Sheets

5,792,173

WOUND CLOSURE HEMOSTASIS DEVICE

BACKGROUND OF THE INVENTION

1. Field of the Invention

This invention relates generally to a wound closure device, and more particularly to compression devices with inflatable balloons to apply sufficient pressure over a wound or blood vessel to stop the flow of blood from the site while permitting blood flow to the site.

2. Description of Related Art

Often it is necessary to very quickly to stop bleeding from an artery during surgery as well as other times when the artery has been nicked. One method of stopping blood flow from the artery is to apply pressure directly to the artery with the use of one's finger.

Mechanical devices for effecting non-invasive compression of arteries include the use of pressure cuffs. Typically, the cuff includes a strip of non-elastic material to be wrapped around a limb. An elastic inflatable bladder is superimposed on the non-elastic material. When the bladder is inflated pressure exerted by all parts of the enwrapment on the limb is increased. U.S. Pat. No. 3,171,410 discloses a pneumatic dressing which exemplifies traditional pressure cuff devices.

Other mechanical devices have been used for decades to achieve hemostasis. Many of these have been based on a C or U-shaped clamp that use a ratcheting effect to allow the operator to apply or release pressure to the puncture site. These clamps have proven to be efficient alternatives to manual compression for control of bleeding after the removal of transfemoral sheaths.

One C-clamp device features a rigid footplate, as disclosed in U.S. Pat. No. 3,799,249 (hereafter the "'249 patent"). The apparatus of the '249 patent is used to exert non-calibrated and unevenly distributed pressure to the body surface overlying an artery. The use of C-clamps can also cause hematomas and they can only be used for a limited time.

U.S. Pat. No. 3,625,219 discloses a transparent rubber membrane clamped to a transparent plastic plate to form an expandable pressure chamber. Clamping screws are used to maintain various members of the chamber support structure in place, and must be loosened to adjust the position of the chamber relative the area to which pressure is to applied.

Further, another type of mechanical device is disclosed in U.S. Pat. No. 4,233,980 (hereafter the "'980 patent"). In the '980 patent an inflatable bladder is formed with two sheets of transparent, non-elastic material that provide lateral restraint. The bladder is inflated by the introduction of a fluid. Vertical expansion is accomplished by the separation of the two sheets of material due to inflation. The bladder is typically mounted on a pressure plate. The pressure plate is mounted on a positioning arm.

It would be desirable to provide a wound closure or hemostasis device which is low cost, and quickly and efficiently applied to a patient. It would also be desirable to provide a wound closure or hemostasis device which uses an inflatable balloon, with provides the function of being an inflatable lens, positioned at the wound site or vessel to stop the bleeding, and which permits viewing of the wound or vessel to position the balloon, and determine when the bleeding has stopped. It would also be desirable to provide a wound closure or hemostatic device which is more comfortable, causes less hematomas and can be used longer than currently available devices.

SUMMARY OF THE INVENTION

Accordingly, it is an object of the present invention to provide a wound closure, hemostasis device that is low cost, and easily attached and deployed to quickly stop bleeding.

A further object of the invention is to provide a wound closure, hemostasis device that uses an inflatable balloon to supply sufficient pressure to stop bleeding at a wound site or at a blood vessel, with the balloon also serving as a lens.

Yet another object of the invention is to provide a wound closure, hemostasis device that utilizes an inflatable balloon to apply a circumferential pressure around the wound site or blood vessel.

Still another object of the invention is to provide a wound closure, hemostasis device which includes a balloon with a toroidal geometry.

Another object of the invention is to provide a wound closure, hemostasis device utilizing a balloon with ribs formed on an interior or exterior surface of the balloon.

Yet another object of the invention is to provide a wound closure, hemostasis device utilizing a balloon with rings formed on an interior or exterior surface of the balloon.

These and other objects of the invention are achieved in a wound closure, hemostasis device with an inflatable balloon with an inflation and deflation outlet. A placement patch includes an aperture for receiving the inflation and deflation outlet. The placement patch has a belt that straps around a patient and holds the placement patch at a desired location. The inflatable balloon is coupled to the placement patch and positioned adjacent to a wound site or a bleeding vessel. An inflation tube, with a proximal and distal end, is coupled at the distal end to the inflation and deflation outlet. Further, an inflation apparatus is coupled to the inflation and deflation outlet.

In another embodiment, the wound closure, hemostasis device balloon has an inflatable section and a non-inflatable section. An inflation apparatus is coupled to the inflatable section.

In a specific embodiment, the apparatus is a femoral hemostat that includes a balloon with an inflation and deflation outlet. The balloon is inflated and deflated by the introduction and expulsion of a gaseous medium. A placement patch has an aperture for receiving the inflation and deflation outlet. The placement patch is positioned with the inflatable balloon adjacent to a femoral puncture site. A retaining member retains the placement patch at a selected position in the vicinity of the puncture site. An inflation tube, with proximal and distal ends, is removeably coupled to the inflation and deflation outlet. An inflation bulb is removeably coupled to the inflation tube proximal end. A regulator valve coupled to the inflation bulb releases gas from the inflatable balloon when a threshold pressure is exceeded.

A belt straps the balloon and placement patch around the patient's body, which is the patient's limb in the case of a femoral hemostat. First and second belt eyelets are formed in the placement patch. Portions of the belt slip through these eyelets so that the belt can be tightened around a patient's limb in order to secure the placement patch and balloon at the puncture site.

The balloon is preferably made of a transparent material permitting positioning and direct visualization of the wound site or blood vessel. The balloon can be made of a flexible material that can withstand a pressure up to about 200 mm Hg. A lens can be formed or positioned at a distal end of the balloon's inflatable section.

The balloon can have a variety of geometrical configurations, including spherical, hemispherical, parabolic, triangular, rectangular, cubic, toroidal, and the like. In the case of a toroidal balloon, pressure is applied circumferentially around the wound or vessel. This causes a pressing together of the tissue which surrounds the would or vessel, causing a closing and stoppage of blood flow.

The balloon can include one or more ribs which can be included in either of an interior balloon surface or an exterior balloon surface. Further, the balloon can also include one or more rings on the interior or exterior surface. The rings are useful for aligning the balloon over the wound or vessel. Optionally included is a heating element, power source and an electrolytic solution positioned in an interior of the inflatable section of the balloon.

In a specific application of the present invention, patients requiring percutaneous transluminal coronary angioplasty on high-risk, or type C lesions, are at 90% risk for coronary artery dissections. Patients with severe, persistent dissection may have less abrupt closure if they are maintained in a therapeutic state of anticoagulation for one month after the procedure. With the use of the present invention, these patients can continue uninterrupted therapeutic-range anticoagulation therapy and have the transfemoral catheter removed safely.

Compared to C-clamps, the present invention is more comfortable and produces fewer hematomas. Because the present invention causes less discomfort, it can be used for longer time periods. This allows additional compression time required to remove transfemoral sheaths in patients receiving therapeutic anticoagulation.

By using a belt to position the placement patch, the practitioner can ensure that pressure is applied continuously during patient transfer or positioning.

DETAILED DESCRIPTION

Figure 1:
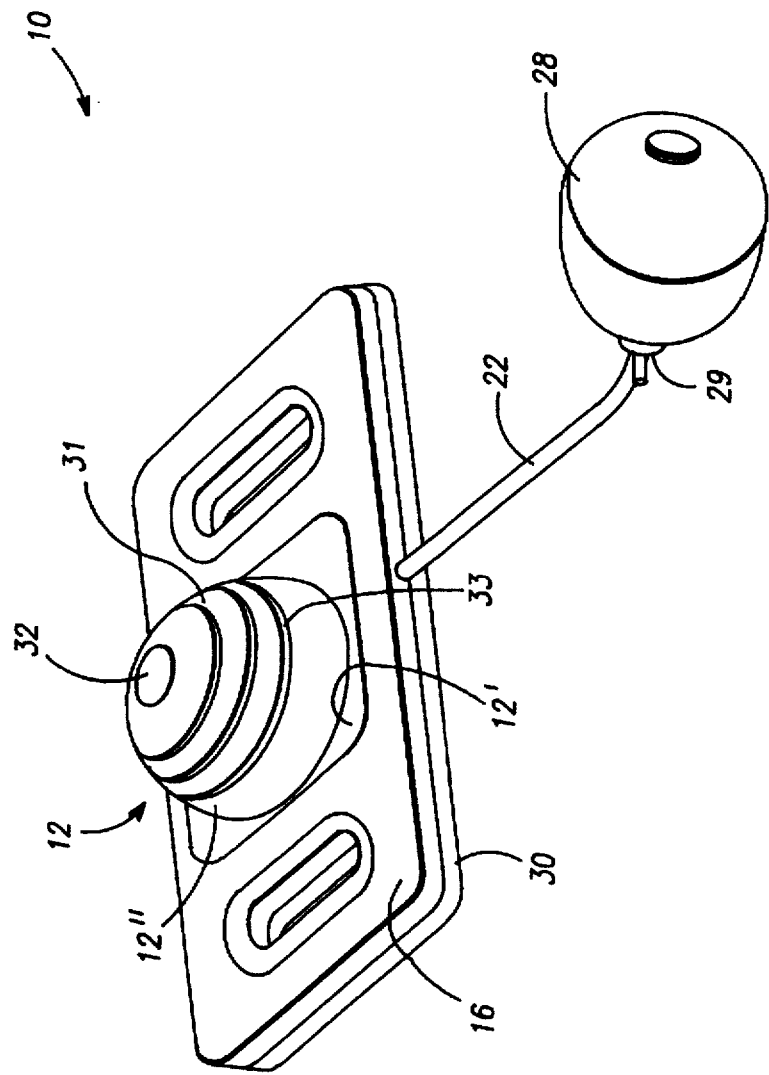
FIG. 1 is a perspective view of the wound closure, hemostasis device of the present invention.
Figure 2:
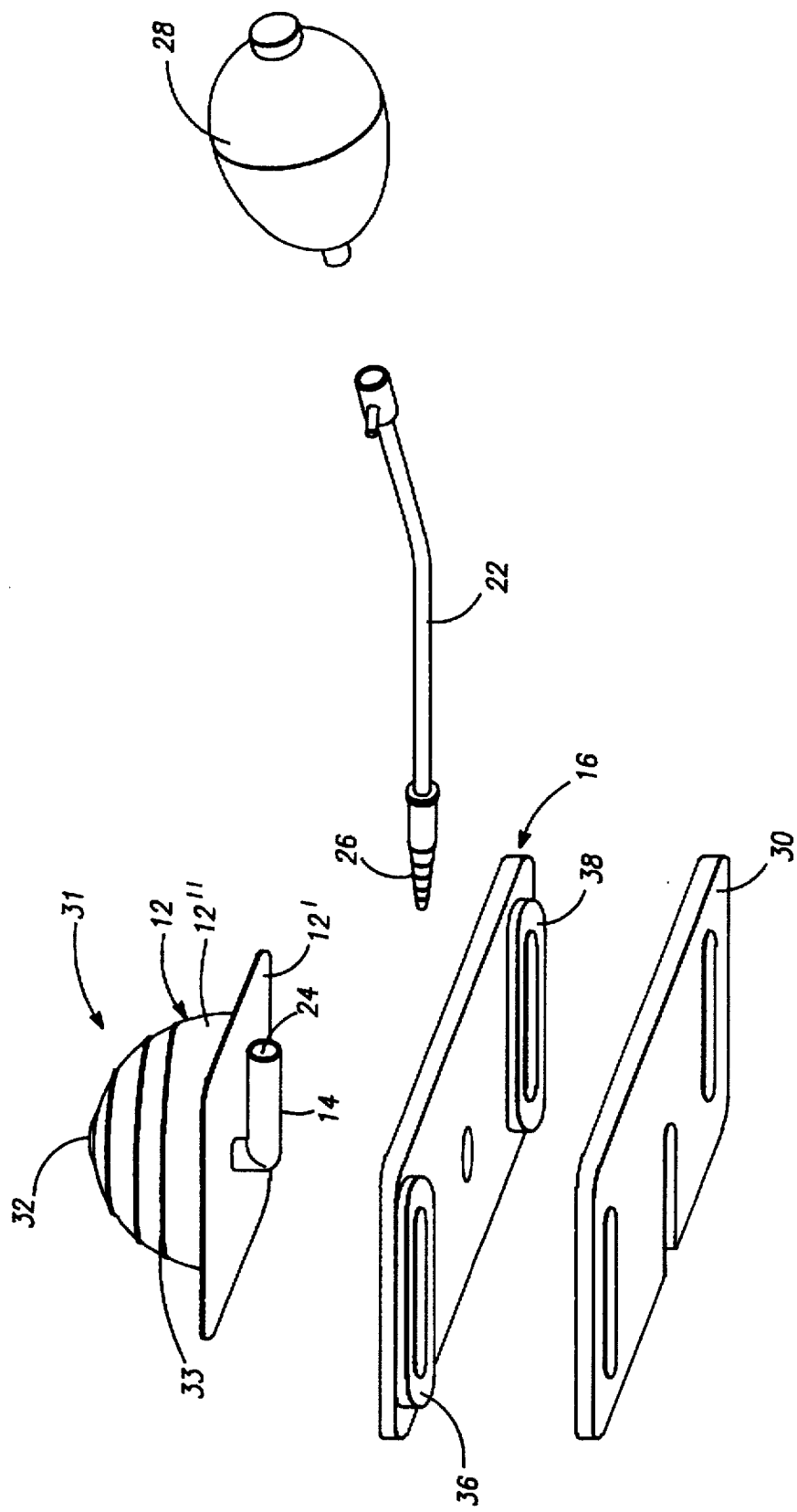
FIG. 2 is an exploded view of the wound closure, hemostasis device of FIG. 1.

Referring now to FIGS. 1 and 2 a wound closure, hemostasis device 10 includes an inflatable balloon 12 with an inflation and deflation outlet 14. Inflatable balloon 12 includes a non-inflatable section 12' and an inflatable section 12". Device 10 can be used to help close wounds and reduce or substantially eliminate the flow of blood out of the wound. Further, device 10 can be a hemostasis device, such as a femoral hemostasis device, used to stop blood flowing from a puncture in a blood vessel. Wound closure, hemostasis device has a variety of different balloon 12 and placement patch 16 sizes suitable for large adults and infants. Different balloon 12 sizes are employed for various vessels and sites, including but not limited to different sizes for brachial and ancillary puncture sites.

Balloon 12 is inflated and stops bleeding at a wound site or bleeding vessel. Although the bleeding stops, blood flow is not shut off which can result in tissue death.

A placement patch 16 has an aperture 18 for receiving inflation and deflation outlet 14. Generally, placement patch 16 has a larger surface area than balloon non-inflatable section 12'. Balloon non-inflatable section 12' is positioned adjacent to placement patch 16. Associated with placement patch 16 is a belt 20 that straps around a patient's body or an appendage such as a limb, finger, and the like, to hold, position or retain placement patch 18 adjacent to a wound site or a bleeding vessel. A distal end of balloon inflatable section 12" is positioned adjacent to the wound site or bleeding vessel. Balloon 12 can be coupled to placement patch 16 detachably or alternatively can be an integral member of placement patch 16.

An inflation tube 22 can be optionally included. A proximal end 24 of inflation and deflation outlet 14 is connected to a distal end 26 of inflation tube 22. Distal end 26 is preferably a luer fitting. Inflatable balloon 12 can be inflated directly without inflation tube 22. An inflation apparatus 28, including but not limited to a manual inflation bulb, foot pump, gas infusion cartridge, e.g., $CO_2$, is used to inflate balloon 12. If inflation apparatus 28 is a bulb, the bulb can be removeably or non-removeably coupled to proximal end 24. Suitable inflation bulbs 28 include but are not limited to aneroid spaygnomarent pumps with male luer fittings. Inflation bulb 28 can be coupled to a regulator valve 29 which releases gas from inflatable balloon 12 when a threshold pressure is exceeded. Alternatively, inflation bulb 28 can include a pressure gauge to indicate the level of pressure in balloon 12.

A backing plate 30 is positioned adjacent to placement patch 16. Backing plate 30 is rigid and not pliable. Because backing plate 30 is rigid, it permits balloon 12 to push against backing plate 30 and the amount of pressure that balloon 12 can sustain is substantially increased.

One or more rings 31 can be formed on one of an interior surface or an exterior surface of balloon 12. In one embodiment, one ring is formed with a 15 mm diameter. Rings are useful visual aids in positioning wound closure, hemostasis device 10 in the proper location relative to a wound or puncture site.

At the distal end of balloon 12 a lens 32 can be positioned. Lens 32 can be formed as an integral part of balloon 12 by varying the thickness of balloon 12 so that it is thickest at its distal end. By carefully controlling the thickness of balloon 12, lens 32, with the desired power, is formed. Lens 32 can magnify the wound site or blood vessel up to about 5 times. This improves the visualization of the site. Additionally, lens 32 can be a separate element and attached to the distal end of balloon 12 after balloon 12 is formed.

One or more ribs 33 can be formed in one of the interior or exterior surfaces of balloon 12. Ribs 33 impart rigidity to balloon 12. Balloon 12 can be formed with one or more chambers, each capable of being inflated to a different pressure level.

One method of creating wound closure, hemostasis device 10 uses a roll of PVC material that is preheated. A preform press and a second press are used to form the different elements of wound closure, hemostasis device 10, with many elements being heat sealed.

Preferably, balloon 12 is made of a material that is transparent. This assists in placing balloon 12 directly over the wound site or punctured vessel permitting continued visualization to determine when blood flow out of the site ceases.

Further, balloon 12 may be made of a material that is flexible and can withstand a pressure of up to 400 mm Hg when inflated. Suitable materials include but are not limited to thermal plastics such as PVC, PT and the like. Typical pressures that are used are in the range of 160 to 200 mm Hg. Factors to be considered in the amount of pressure to use are if a backing plate is positioned on one side of placement patch 16, the patient's distal blood pressure and the use of anti-coagulants. The addition of a backing plate increases up to 50 times the possible pressures that balloon 12 can withstand.

Figure 5:
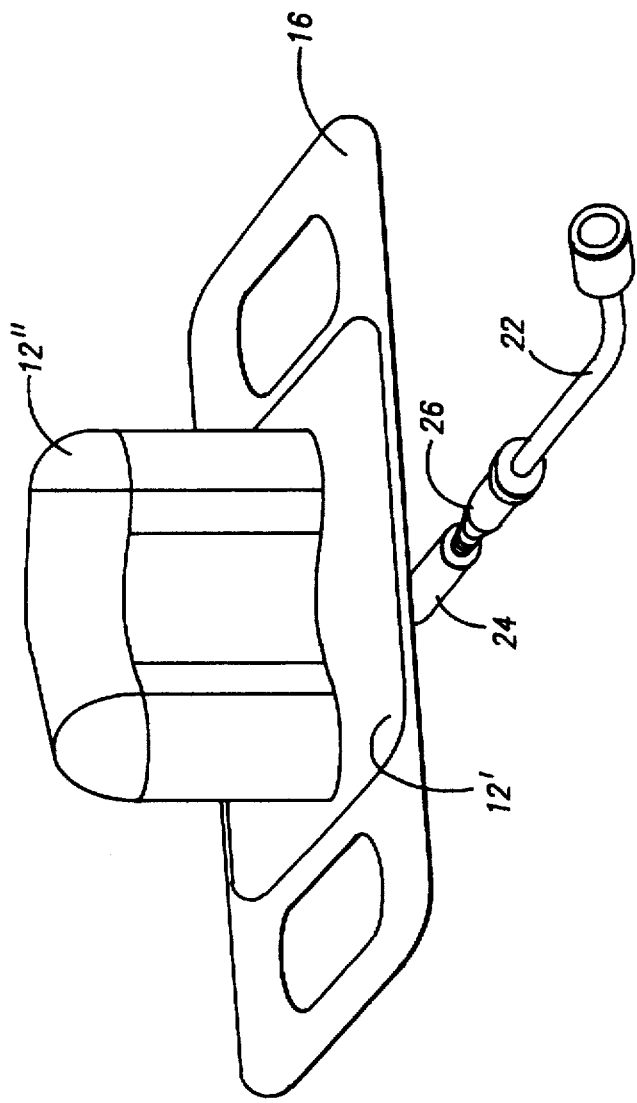
FIG. 5 is a perspective view of a wound closure, hemostasis device using a kidney-shaped balloon.
Figure 6:
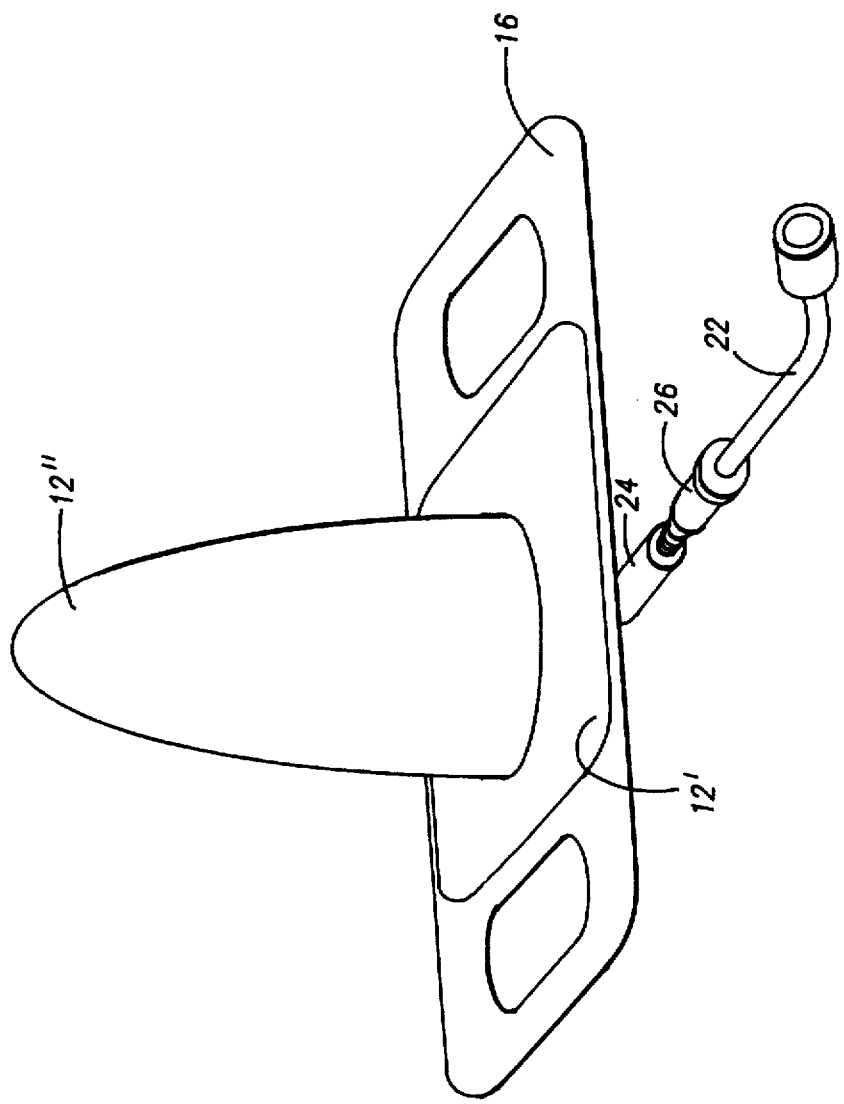
FIG. 6 is a perspective view of a wound closure, hemostasis device using a tapered-cone-shaped balloon.
Figure 7:
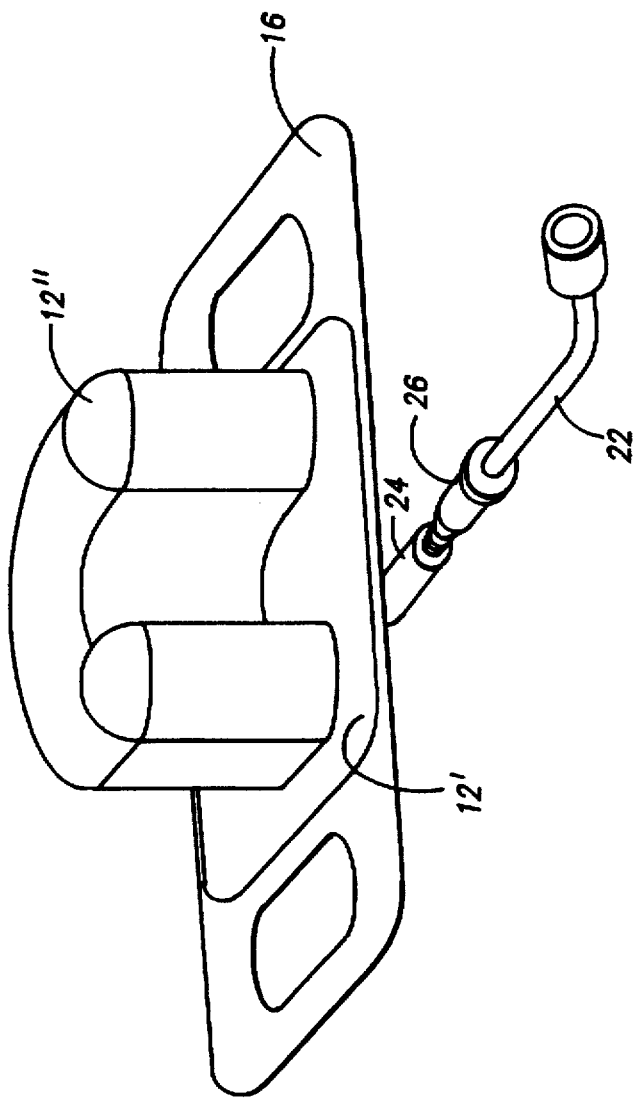
FIG. 7 is a perspective view of a wound closure, hemostasis device using a horseshoe-shaped balloon.
Figure 8:
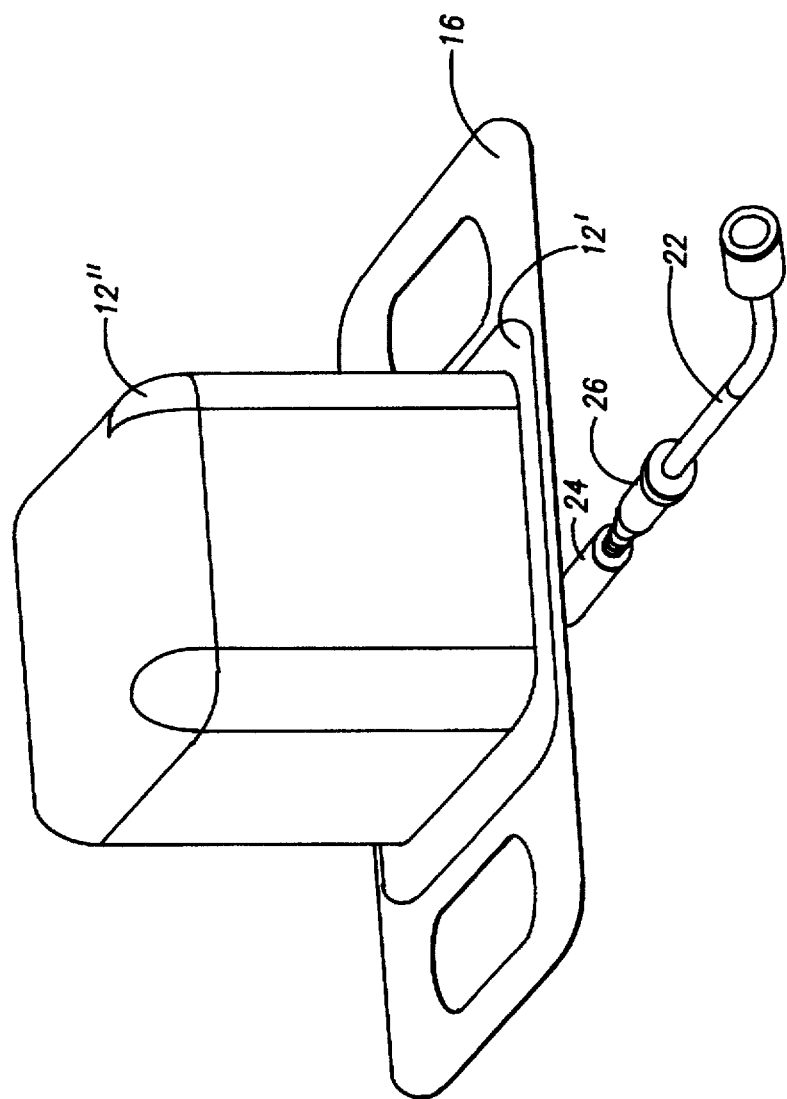
FIG. 8 is a perspective view of a wound closure, hemostasis device using a square-shaped balloon.
Figure 9:
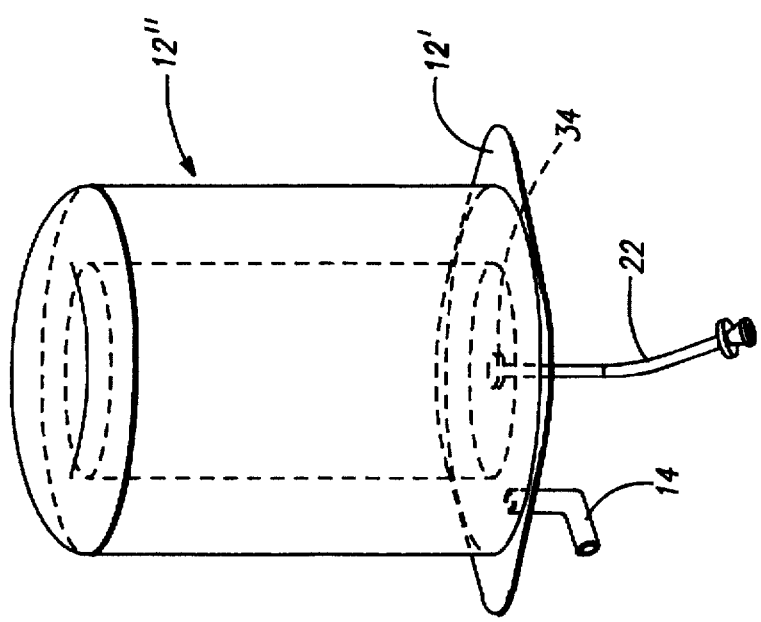
FIG. 9 is a perspective view of a wound closure, hemostasis device using a cylindrical-shaped balloon that is particularly suitable for amputated limbs.

Balloon inflatable section 12" can have a variety of geometric configurations, including but not limited to spherical and non-spherical. Some of these configurations include a toroid (FIGS. 3 and 4), kidney-shaped (FIG. 5), tapered cone (FIG. 6), horseshoe (FIG. 7), square (FIG. 8), and cylindrical (FIG. 9). A cylindrical geometry is particularly suitable for use with amputated limbs. The long cylindrical geometry encloses the amputated limb and applies sufficient pressure to stop bleeding without cutting off blood flow to the limb.

Figure 3:
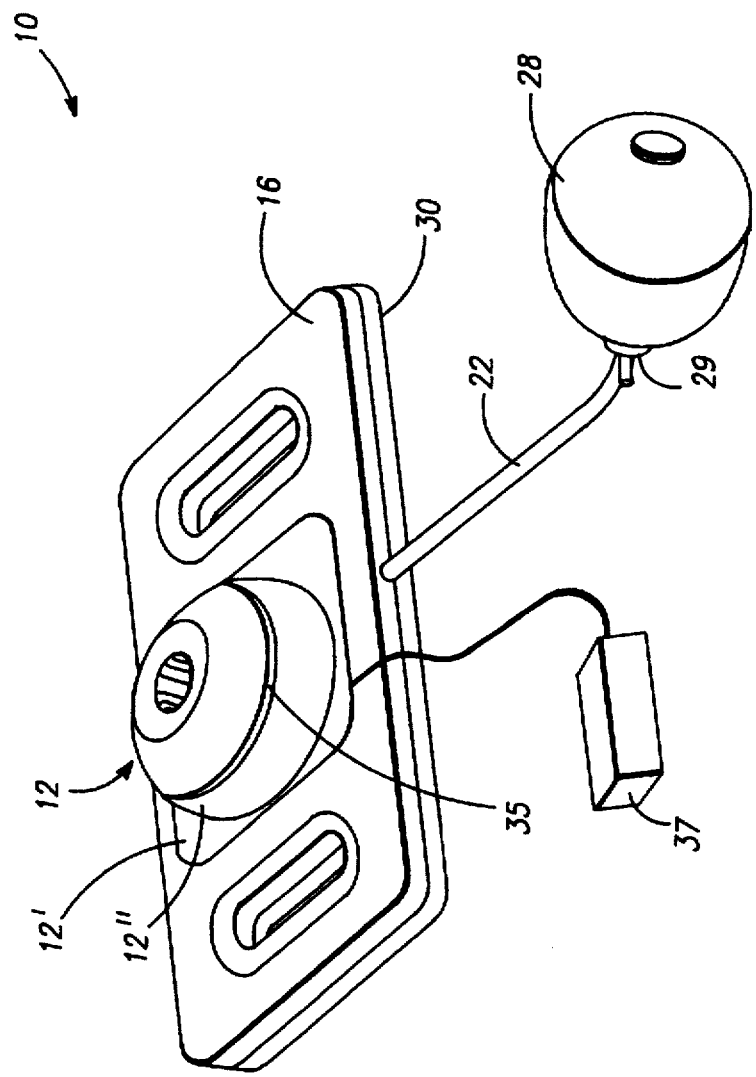
FIG. 3 is a perspective view of a wound closure, hemostasis device using a toroidal shaped balloon.
Figure 4:
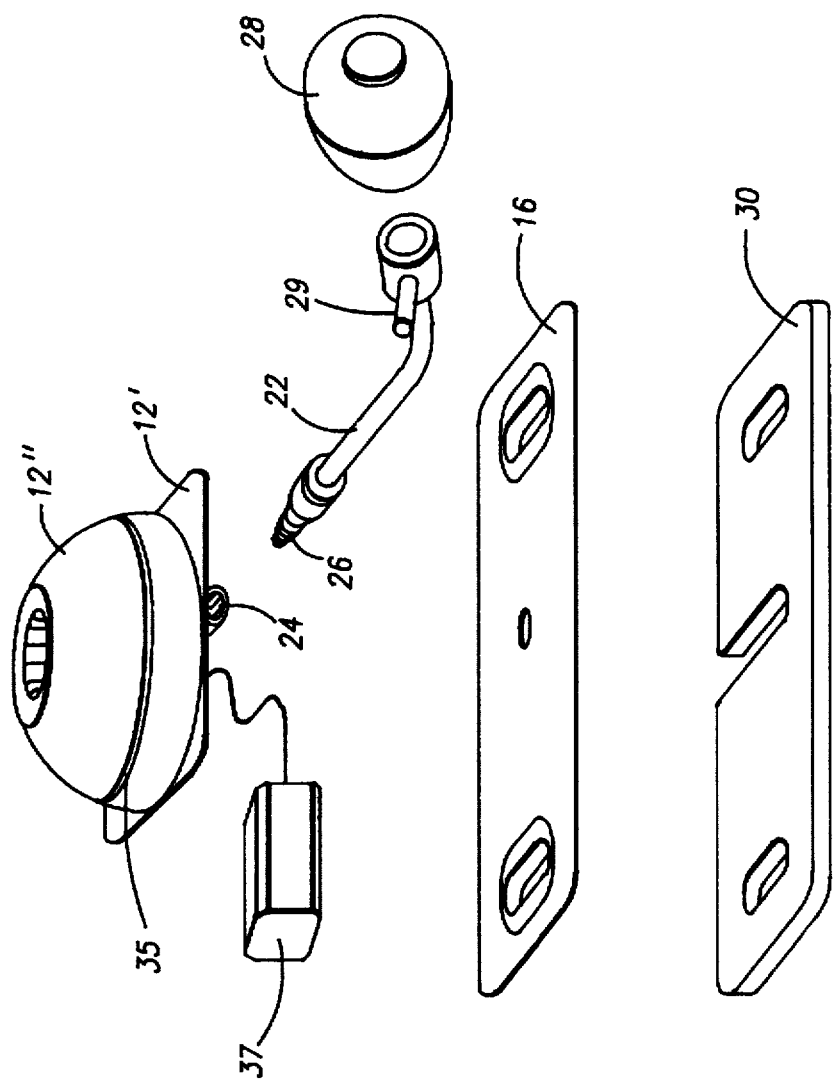
FIG. 4 is an exploded view of the would closure, hemostasis device of FIG. 3.

FIGS. 3 and 4 illustrate that a heating element 35 can be disposed on an interior or an exterior surface of balloon inflatable section 12", or positioned in an interior of balloon inflatable section 12". Heating element 35 can be a small wire, including but not limited to an RF antenna, and produces an electromagnetic field which aids in hemostasis and promotes wound healing. A power source 37, such as one or more batteries or other energy source, is coupled to heating element 35. Power source 37 can be positioned on belt 20, placement patch 16 and the like. Further, an electrolytic solution can be housed in the interior of balloon inflatable section 12'. Electrolytic solution increases the strength of electromagnetic field in the interior of inflatable balloon section 12" and provides a greater heating effect at the wound or bleeding vessel site. Although heating element 35 is shown as being associated with the toroid geometry of FIGS. 3 and 4, heating element 35 can be used with any geometry of balloon inflatable section 12".

Figure 11:
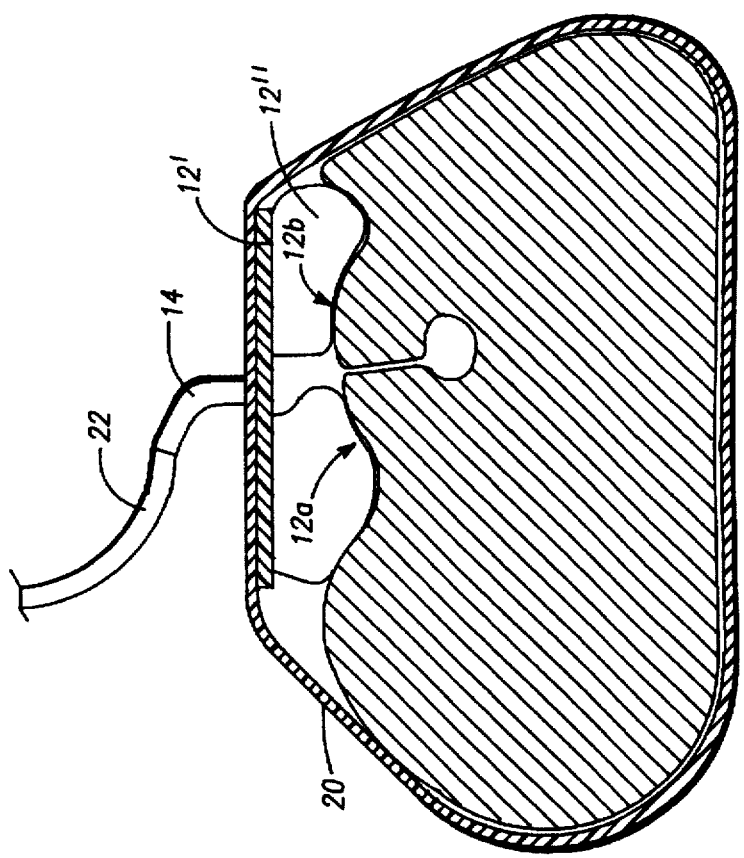
FIG. 11 is a cross-sectional view of a wound closure, hemostasis device of the present invention with a toroidal-shaped balloon in an inflated state applying sufficient pressure to the tissue surrounding the wound site to substantially close the wound site.
Figure 10:
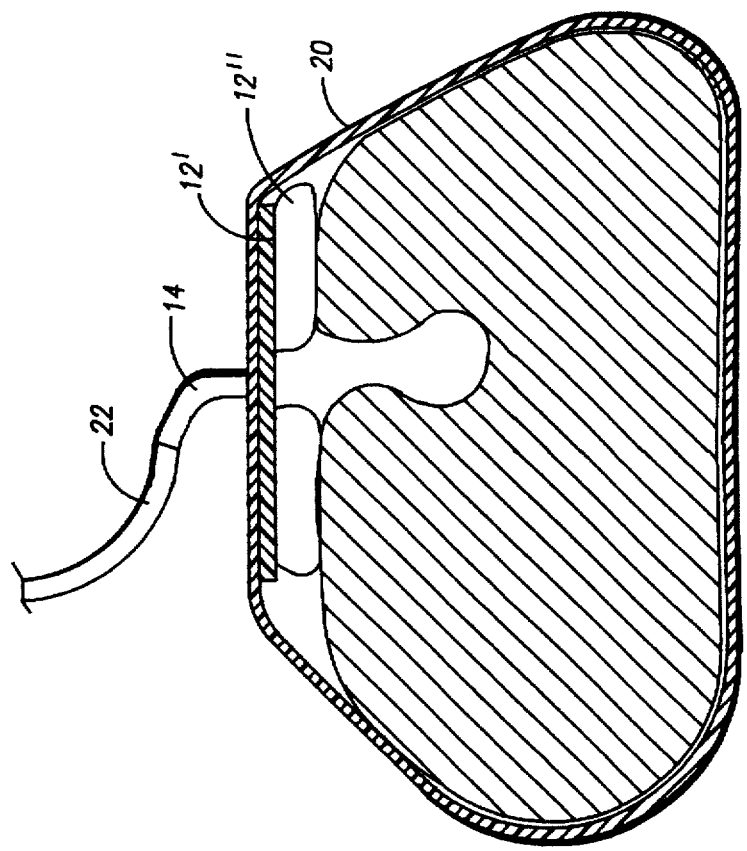
FIG. 10 is a cross-sectional view of a wound closure, hemostasis device of the present invention with a toroidal-shaped balloon in its non-inflated state applied to a wound site.

A cross-sectional view of a toroidal balloon 12 is illustrated in FIGS. 10 and 11. Toroidal-shaped balloon 12 is positioned adjacent to the wound site. Balloon inflatable section 12" becomes inflated and begins to exert a force (illustrated as 12(a)) around a periphery of the wound site. As balloon inflatable section 12" becomes inflated, the force applied around the periphery of the wound increases. In certain instances balloon 12 can close the wound site. As the amount of wound closure increases the wound healing process is enhanced.

Balloon non-inflatable section 12' can be a bag, or membrane, that includes a resealable injection port 34 (FIG. 9). After balloon inflatable section 12" is inflated around a limb, wound site or blood vessel, resealable injection port 34 can be used to introduce medication, sterile solutions, or irrigation.

Belt 20 straps around a patients's body or limb. Belt 20 is adjustable in order to fit around limbs of various sizes. Eyelets are formed in placement patch 16 for receiving belt 20. Reinforcement structures 36 and 38 (FIG. 2) can be formed around the peripheries of the eyelets. Reinforcement members 36 and 38 add additional strength to placement patch 16 when belt 20 is cinched around a patient's limb, and separate placement patch 16 from backing plate 30. Suitable materials which can be used for reinforcement members 36 and 38 include but are not limited to thermal plastics. Belt 20 can be fastened with Velcro, spring loaded clips and the like.

Placement patch 16 can be of a variety of sizes. In one embodiment, it is 7.8 inches in length and has a width of 4.3 inches. Placement patch 16 can be made of a variety of materials including but not limited to thermal plastics. Placement patch 16 and balloon 12 can be formed as one integral unit. Balloon 12 can also be detachably coupled to placement patch 16. Further, two or more balloons 12 can be included on placement patch 16, or on numerous placement patches, all in one device. Inflation tube 22 can also be integrally formed with placement patch 16 and balloon 12. Alternatively, inflation tube 22 can be detachable from inflation and deflation outlet 14. Further, belt 20 can also be an integral element with placement patch 16.

In one embodiment, hemostasis pressure device 10 is a femoral hemostat 10 that includes balloon 12 with inflation and deflation outlet 14. Balloon 12 is inflated and deflated by the introduction and expulsion of a gaseous medium. Placement patch 16 has aperture 18 for receiving inflation and deflation outlet 14. Placement patch 16 is positioned with inflatable balloon 12 adjacent to a femoral puncture site. Belt 20 retains placement patch 16 at a selected position in the vicinity of the puncture site. Inflation tube 22 is removably coupled to inflation and deflation outlet 14. Inflation bulb 28 is removably coupled to inflation tube proximal end 24. Regulator valve 29, if included, is coupled to inflation bulb 28 and releases gas from inflatable balloon 12 when a threshold pressure is exceeded.

In another embodiment, wound closure, hemostasis device 10 can be used to control bleeding after removal of transfemoral sheaths and devices. Belt 20 is first positioned under the patient's hips or limbs in a manner that places belt 20 directly in line with the puncture site or sites. The puncture site is located and balloon inflatable section 12" is positioned over and slightly superior and medial to the puncture site. The hub of an arterial sheath protrudes past the edge of dome 12(a). It may be necessary to partially pull back the arterial sheath to this position. Belt 20 is tightened so that placement patch 16 is pressed tightly against the skin surface. This ensures that dome 12(a) is positioned correctly. Bulb 28 is attached to distal end 26. Pressure is applied in the range of 20 to 30 mm Hg for a venous sheath, and the sheath is removed. The pressure is then increased to about 60 to 80 mm Hg and the arterial sheath is removed. Pressure is increased until it reaches 10 to 20 mm Hg grater than the patient's systolic blood pressure, or until hemostasis is achieved.

In a general embodiment, balloon 12 is inflated until hemostasis is achieved. That pressure is maintained about 30 to 45 minutes. Pressure is then decreased by 10 mm Hg every 10 minutes. This reduces changes of anemia and dissection.

In another embodiment, once hemostasis is achieved, the amount of pressure is gradually reduced to a level that allows for a palpable pedal pulse while still controlling bleeding after hemostasis has been achieved. Pressure is applied for a period to be determined by the condition of the artery. The puncture site is carefully observed. Pressure is slowly released in decrements of 10 to 20 mm Hg every 2 to 3 minutes. If bleeding recurs, pressure is increased until it stops.

Femoral hemostat 10 can be utilized in substantially any emergency condition whenever the femoral artery is punctured. While it is frequently the case during surgery that suddenly an artery is punctured, it is not unusual for a nurse or physician to plug the puncture site with a finger. Femoral hemostat 10 can be utilized in this instances and is quickly and efficiently positioned around the limb. Thereafter, balloon 12 is properly positioned at the puncture site and inflated. The practitioner uses inflation apparatus 28 to apply sufficient gas to balloon 12 so the bleeding stops. When inflation apparatus 28 is a bulb, regulator valve 29 automatically releases pressure from balloon 12 when too much pressure has been applied. Belt 20 can include Velcro components, or alternatively a buckle, in order to press placement patch 16 firmly against the skin. Belt 20 can be readjusted until placement patch 16 is properly positioned. A bilateral buckle can be used for bilateral femoral puncture sites.

Patients requiring percutaneous transluminal coronary angioplasty on high-risk, or type C lesions, are at 90% risk for coronary artery dissections. Patients with severe, persistent dissection may have less abrupt closure if they are maintained in a therapeutic state of anticoagulation for one month after the procedure. With the use of hemostasis pressure device 10, these patients can continue uninterrupted therapeutic-range anticoagulation therapy and have the transfemoral catheter removed safely.

Compared to C-clamps, hemostasis pressure device 10 is more comfortable, produces fewer hematomas. Because hemostasis pressure device 10 causes less discomfort, it can be used for longer time periods. This allows additional compression time required to remove transfemoral sheaths in patients receiving therapeutic anticoagulation.

By using belt 20 to position placement patch 16, the practitioner can ensure that pressure is applied continuously during patient transfer or positioning.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A wound closure, hemostasis device, comprising:
  a balloon with a distal end, an inflation and deflation outlet, an inflatable section and a non-inflatable section extending outward from a periphery of the inflatable section;
  a placement patch configured to accommodate balloons of different geometries, and including an aperture for receiving the inflation and deflation outlet, wherein the non-inflatable section of the inflatable balloon is removably coupled to the placement patch;
  an attachment mechanism coupled to the placement patch and configured to be strapped around one of a patient's body or a patient's appendage and hold the placement patch adjacent to one of a wound site or a bleeding vessel; and
  an inflation apparatus coupled to the inflation and deflation outlet.

2. The wound closure, hemostasis device of claim 1, wherein the balloon has a geometry which applies pressure around a periphery of one of the wound site or bleeding vessel and pinches surrounding tissue together.

3. The wound closure, hemostasis device of claim 1, wherein the balloon has at least a section with a spherical geometry.

4. The wound closure, hemostasis device of claim 1, wherein the balloon has at least a section with a non-spherical geometry.

5. The wound closure, hemostasis device of claim 4, wherein the balloon has at least a section with a toroidal geometry.

6. The wound closure, hemostasis device of claim 1, wherein the balloon applies a circumferential pressure around one of the wound site or the bleeding vessel.

7. The wound closure, hemostasis device of claim 1, wherein the balloon has a lens on a distal end of the balloon formed as an integral part of the balloon.

8. The wound closure, hemostasis device of claim 7, wherein the balloon is made of a transparent material, and the lens permits improved viewing of one of the wound site or bleeding vessel.

9. The wound closure, hemostasis device of claim 1, wherein the balloon includes one or more ribs formed on one of an internal or external surface of the balloon.

10. The wound closure, hemostasis device of claim 1, wherein the balloon includes one or more rings formed on one of an interior or exterior surface of the balloon.

11. The wound closure, hemostasis device of claim 1 further comprising,
  a backing plate coupled to the placement patch supplying sufficient support for the balloon and allowing the balloon to be inflated to larger pressures.

12. The wound closure, hemostasis device of claim 1, wherein the non-inflatable section has an integrally formed injection port.

13. The wound closure, hemostasis device of claim 1, wherein the inflatable section has a geometry with a hollow center, and an injection port is positioned adjacent to the hollow center.

14. The wound closure, hemostasis device of claim 1, further comprising:
  a heating element, configured to be coupled to a power source, positioned in one of a surface of the balloon or in an interior of the balloon.

15. The wound closure, hemostasis device of claim 14, further comprising:
  a power source connected to the heating element.

16. The wound closure, hemostasis device of claim 15, wherein the power source is one or more batteries positioned on one of the attachment mechanism or placement patch.

17. The wound closure, hemostasis device of claim 14, further comprising:
  an electrolytic solution positioned in the interior of the balloon.

18. The wound closure, hemostasis device of claim 14, wherein the heating element is an RF antenna.

19. The wound closure, hemostasis device of claim 1, wherein the balloon is made of a plurality of membranes.

20. The wound closure, hemostasis kit of claim 1, wherein the balloon has a lens on a distal end of the balloon formed as a lens that is non-integral with the balloon and applied to the balloon's distal end.

21. The wound closure, hemostasis device of claim 20, wherein the balloon is made of a transparent material, and the lens permits improved viewing of one of the wound site or bleeding vessel.

22. A wound closure, hemostasis kit, comprising:

a plurality of balloons, each balloon having a distal end, an inflatable section, a non-inflatable section and an inflation and deflation outlet, the inflatable section of each balloon having a different lateral cross-section geometry;

a placement patch configured to be removably coupled to the non-inflatable section of each balloon;

an attachment mechanism coupled to the placement patch configured to be strapped around a patient to hold the placement patch adjacent to one of a wound site or a bleeding vessel.

23. The wound closure, hemostasis kit of claim 22, further comprising an inflation apparatus coupled to the inflation and deflation outlet and the inflation apparatus is a hand operated bulb with a regulator valve coupled to the inflation bulb.

24. The wound closure, hemostasis kit of claim 22, wherein at least one balloon inflatable section has a geometry which applies pressure around a periphery of one of the wound site or the bleeding vessel and pinches surrounding tissue together.

25. The wound closure, hemostasis kit of claim 22, wherein at least one balloon inflatable section has at least a section with a spherical geometry.

26. The wound closure, hemostasis kit of claim 22, wherein at least one balloon inflatable section has at least a section with a non-spherical geometry.

27. The wound closure, hemostasis kit of claim 26, wherein at least one balloon inflatable section has at least a section with a toroidal geometry.

28. The wound closure, hemostasis kit of claim 22, wherein at least one balloon inflatable section applies a circumferential pressure around one of the wound site or the bleeding vessel.

29. The wound closure, hemostasis kit of claim 22, wherein at least one balloon includes a lens at the distal end of the balloon inflatable section.

30. The wound closure, hemostasis kit of claim 29, wherein the lens is formed integrally with the balloon inflatable section.

31. The wound closure, hemostasis kit of claim 29, wherein the lens is a separate element which is not integrally formed with the balloon inflatable section.

32. The wound closure, hemostasis kit of claim 29, wherein at least one balloon is made of a transparent material, and the lens permits improved viewing of one of the wound site or bleeding vessel.

33. The wound closure, hemostasis kit of claim 22, wherein at least one balloon includes one or more ribs formed on one of an internal or external surface of the balloon.

34. The wound closure, hemostasis kit of claim 22, wherein at least one balloon includes one or more rings formed on one of an interior or exterior surface of the balloon.

35. The wound closure, hemostasis kit of claim 22, further comprising, a backing plate coupled to the placement patch supplying sufficient support to the placement patch to allow the balloon to be inflated to larger pressures.

36. The wound closure, hemostasis kit of claim 22, wherein at least one balloon non-inflatable section is a non-inflatable bag with an injection port.

37. The wound closure, hemostasis kit of claim 36, wherein at least one balloon inflatable section has a geometry with a hollow center, and the injection port is positioned adjacent to the hollow center.

38. The wound closure, hemostasis kit of claim 22, further comprising:

a heating element positioned on one of a surface of at least one balloon inflatable section or in an interior of at least one balloon inflatable section.

39. The wound closure, hemostasis kit of claim 38, further comprising:

a power source connected to the heating element.

40. The wound closure, hemostasis kit of claim 39, wherein the power source is one or more batteries positioned on one of the belt or placement patch.

41. The wound closure, hemostasis kit of claim 38, further comprising:

an electrolytic solution positioned in the interior of the balloon.

42. The wound closure, hemostasis kit of claim 38, wherein the heating element is an RF antenna.

43. The wound closure, hemostasis kit of claim 22, wherein at least one balloon inflatable section is made of a plurality of membranes.

* * * * *